United States Patent
Andersen et al.

(10) Patent No.: US 10,207,927 B2
(45) Date of Patent: Feb. 19, 2019

(54) METHOD TO PRODUCE A CALIBRATION, REAGENT OR THERAPEUTIC GAS BY EXPOSING A PRECURSOR GAS TO ULTRAVIOLET LIGHT

(75) Inventors: Peter C. Andersen, Superior, CO (US); Craig J. Williford, Golden, CO (US); John W. Birks, Boulder, CO (US)

(73) Assignee: LUDLUM MEASUREMENTS, INC., Sweetwater, TX (US)

( * ) Notice: Subject to any disclaimer, the term of this patent is extended or adjusted under 35 U.S.C. 154(b) by 1232 days.

(21) Appl. No.: 12/595,930

(22) PCT Filed: Apr. 25, 2008

(86) PCT No.: PCT/US2008/061535
§ 371 (c)(1),
(2), (4) Date: Oct. 14, 2009

(87) PCT Pub. No.: WO2008/134490
PCT Pub. Date: Nov. 6, 2008

(65) Prior Publication Data
US 2010/0108489 A1    May 6, 2010

Related U.S. Application Data

(60) Provisional application No. 60/914,087, filed on Apr. 26, 2007.

(51) Int. Cl.
*C01B 7/20* (2006.01)
*A61K 33/00* (2006.01)
(Continued)

(52) U.S. Cl.
CPC .............. *C01B 21/24* (2013.01); *A61K 33/00* (2013.01); *B01J 19/123* (2013.01); *C01B 7/20* (2013.01);
(Continued)

(58) Field of Classification Search
CPC ........... C01B 21/24; C01B 31/18; C01B 7/20; C01B 32/40; A61K 33/00; B01J 19/123; B01J 2219/0875; B01J 2219/0869
(Continued)

(56) References Cited

U.S. PATENT DOCUMENTS 3,113,086 A * 12/1963 Taylor ........................ 204/157.5
3,853,790 A    12/1974 Vosolsobe et al.
(Continued)

FOREIGN PATENT DOCUMENTS

DE        2211720 A  *  3/1972

OTHER PUBLICATIONS

Doering and Mahan, "Photolysis of Nitrous Oxide. II. 1470 and 1830 A," J. Chem. Phys. 36, pp. 1682-1687 (1962).*
(Continued)

*Primary Examiner* — Nicholas A Smith
*Assistant Examiner* — Colleen M Raphael
(74) *Attorney, Agent, or Firm* — Polson Intellectual Property Law P.C.; Margaret Polson; Christopher Sylvain

(57) ABSTRACT

The present invention provides a means of producing nitric oxide (NO) by photolysis of nitrous oxide ($N_2O$) at ultraviolet wavelengths. One application is the production of a known concentration of NO in a diluent gas for calibration of analytical instruments that measure nitric oxide in gases such as exhaled breath, ambient air and automobile exhaust. A potentially important medical application is the production of NO for inhalation therapy, an advantage being that very little toxic $NO_2$ gas is produced. The method is useful for producing NO for industrial applications as well. Advantages of this method of NO production include the use of a single, inexpensive, readily available reagent gas of very low toxicity. Furthermore, the concentration of NO produced can be easily controlled by varying the ultraviolet
(Continued)

(UV) lamp intensity and relative gas flow rates. The method may also be applied to the production of controlled concentrations of other gases as well such as CO and $F_2$ by using reagent gases other than $N_2O$.

28 Claims, 3 Drawing Sheets

(51) Int. Cl.
*B01J 19/12* (2006.01)
*C01B 21/24* (2006.01)
*C01B 32/40* (2017.01)

(52) U.S. Cl.
CPC ....... *C01B 32/40* (2017.08); *B01J 2219/0869* (2013.01); *B01J 2219/0875* (2013.01)

(58) Field of Classification Search
USPC .......................................... 204/157.46, 157.5
See application file for complete search history.

(56) References Cited

U.S. PATENT DOCUMENTS

| | | | |
|---|---|---|---|
| 3,948,610 A | | 4/1976 | Sutcliffe et al. |
| 3,984,296 A | * | 10/1976 | Richards ................. 204/157.46 |
| 3,993,911 A | * | 11/1976 | Graentzel ................. 422/186.3 |
| 4,167,463 A | * | 9/1979 | Conrad ................... 204/157.46 |
| 4,272,336 A | | 6/1981 | Vayenas et al. |
| 4,774,069 A | | 9/1988 | Handley |
| 4,812,300 A | | 3/1989 | Quinlan et al. |
| 5,396,882 A | | 3/1995 | Zapol |
| 5,478,549 A | | 12/1995 | Koch |
| 5,670,127 A | | 9/1997 | Sheu |
| 5,683,668 A | | 11/1997 | Hrabie et al. |
| 5,692,495 A | | 12/1997 | Sheu |
| 5,827,420 A | | 10/1998 | Shirazi et al. |
| 6,103,275 A | | 8/2000 | Seitz et al. |
| 6,159,421 A | | 12/2000 | Fujii |
| 6,534,029 B1 | | 3/2003 | Klein et al. |
| 6,690,112 B2 | | 2/2004 | Wood et al. |
| 6,743,404 B1 | | 6/2004 | Schumacher et al. |
| 6,758,214 B2 | | 7/2004 | Fine et al. |
| 7,025,869 B2 | | 4/2006 | Fine et al. |
| 7,040,313 B2 | | 5/2006 | Fine et al. |
| 7,048,951 B1 | | 5/2006 | Seitz et al. |
| 2004/0108197 A1 | * | 6/2004 | Buhr ....................... 204/157.15 |
| 2005/0035711 A1 | * | 2/2005 | Spielman et al. ............ 313/567 |
| 2007/0215454 A1 | * | 9/2007 | Sotoaka et al. .......... 204/157.46 |

OTHER PUBLICATIONS

Doering and Mahan, "Photolysis of Nitrous Oxide. I. 1236 Å," J. Chem. Phys. 34, pp. 1617-1620 (1961).*

Yang and Servedio, "Photolysis of Nitrous Oxide at 1470 Å," J. Chem. Phys. 47, pp. 4817-4819 (1967).*

Mahan, "Photolysis of Carbon Dioxide," J. Chem. Phys. 33, pp. 959-965 (1960).*

Groth, W.E. and H. Schierholz, "The Photolysis of Nitrous Oxide in the Far Ultraviolet." vol. 1 of Planetary and Space Science 1959: p. 333-342.

Hampson, Jr., Edward and David Garvin, eds., Nat'l Measurement Laboratory, U.S. Department of Commerce, Reaction Rate and Photochemical Data for Atmospheric Chemistry 27 (1977).

Wine, P.H. and A.R. Ravishankara, "Photolysis at 248 nm and O(1D2) Quenching by H20, CH4. H2 and N20: O (3PJ) Yields." vol. 69 of Chemical Physics 1982: 365-373.

Nat'l Aeronautics and Space Administration, Chemical Kinetics and Photochemical Data for Use in Atmospheric Studies Evaluation No. 15 4-31-32 (2006).

International Search Report and Written Opinion, International Application No. PCT/US2008/061535, dated Sep. 23, 2008 for Applicant 2B Technologies, Inc., 10 pages.

International Preliminary Examination Report for related application PCT/US2008/061535, dated Mar. 22, 2010.

Groth, W.E. and H. Schierholz, "The Photolysis of Nitrous Oxide in the Far Ultraviolet", Planet Space. Sci., Pergamon Press 1959, vol. 1 pp. 333-342.

* cited by examiner

METHOD TO PRODUCE A CALIBRATION, REAGENT OR THERAPEUTIC GAS BY EXPOSING A PRECURSOR GAS TO ULTRAVIOLET LIGHT

BACKGROUND

Nitric oxide (NO) is used in numerous commercial and industrial applications. As a raw material it is used in the semiconductor industry for surface oxidation processes. As a synthesis gas, NO is used in the preparation of nitric acid, hydroxylamine, nitrosyl chloride, metal nitrosyls, and caprolactam, which is used in the synthesis of nylon. Nitric oxide is also used commercially as a polymerization inhibitor during the preparation of olefins and to modify the properties of various polymers.

Several processes have been developed for the preparation of nitric oxide. Commercially, NO is produced by the Ostwald process in which ammonia is oxidized at temperatures near 800° C. in the presence of a platinum group catalyst. Nitric oxide can also be produced from the reaction of nitric acid and copper or the reaction of sodium nitrate and sulfuric acid. These methods are not convenient for small scale NO production due to the power requirements for heating the reaction mixtures to several hundred degrees Celsius and the hazards inherent in handling strong acids. Several processes have been proposed for bench-scale production of nitric oxide for on-site use in laboratories, production facilities and medical facilities. Attention is directed to U.S. Pat. Nos. 3,853,790; 3,948,610; 4,272,336; 4,774,069; 4,812,300; 5,396,882; 5,478,549; 5,670,127; 5,683,668; 5,692,495; 5,827,420; 6,103,275; 6,534,029; 6,743,404; 6,758,214; 7,025,869; 7,040,313 and 7,048,951. Each of these methods has disadvantages relative to the photolysis of nitrous oxide ($N_2O$). For example, some require toxic starting materials or produce toxic byproducts such as nitrogen dioxide ($NO_2$), while others require high temperatures, high voltages or use of strong acids.

In the analysis of air and other gases for nitric oxide, it is necessary to calibrate the analytical instrument using a gas standard having a known concentration of NO. The most common method used for NO detection is based on chemiluminescence in the reaction of NO with an excess of ozone. The method, which is widely used for air pollution monitoring, for measurements of NO in automobile exhaust and for measurements of NO in exhaled breath, requires frequent calibration with a standard gas mixture. Nitric oxide measurements based on electrochemical techniques, chemiluminescence with luminol and other methods require calibration using a gas standard as well.

A well known problem with NO gas standards is that NO is unstable in gas cylinders at low concentrations; when NO standards are prepared at part-per-billion by volume (ppbv) levels there is a strong tendency for the concentration of NO in the cylinder to decline with time even though the NO is diluted into an unreactive gas such as nitrogen. One reason for this is that NO is thermodynamically unstable with respect to disproportionation to form $N_2O$ and $NO_2$ according to the equilibrium:

$$3NO \rightleftharpoons N_2O + NO_2 \quad (3)$$

Although extremely slow in the gas phase, this reaction may be catalyzed on the interior walls of compressed gas cylinders. The walls may be treated in various ways to slow the reaction, but the treatment is not always effective, and one cannot be certain that the concentration of NO in a gas cylinder is what it was when the cylinder was first filled.

Furthermore, even trace amounts of oxygen ($O_2$) in the diluent gas can react to oxidize NO to $NO_2$ according to the well known reaction:

$$2NO + O_2 \rightarrow 2NO_2 \quad (4)$$

Also, because of reaction 4, NO compressed gas standards cannot be made with air as the diluent. This is a disadvantage since it is desirable to calibrate an NO instrument using the same diluent gas as the gas being analyzed, which is most commonly air.

Nitric oxide standards are much more stable at high concentrations of NO; thus, it is common to prepare gas standards at the high ppmv level in an unreactive gas such as $N_2$ to make a compressed gas standard and then dynamically dilute that standard with $N_2$ or air prior to entering the analytical instrument being calibrated. Although the dynamic dilution method works well for calibration, flow meters are required, and the flow meters must be accurately calibrated, thus adding to the complexity, expense and uncertainty of the calibration procedure.

Nitric oxide has several medical applications. Blood vessels use nitric oxide to signal the surrounding smooth muscle to relax, thus dilating the artery and increasing blood flow. This underlies the action of nitroglycerin, amyl nitrate and other nitrate derivatives in the treatment of heart disease; the compounds undergo reactions that release nitric oxide, which in turn dilates the blood vessels around the heart, thereby increasing its blood supply.

Some disorders or physiological conditions can be mediated by inhalation of nitric oxide. Dilation of pulmonary vessels in the lungs due to inhaled NO causes pulmonary gas exchange to be improved and pulmonary blood flow to be increased. The administration of low concentrations of inhaled nitric oxide can prevent, reverse, or limit the progression of disorders such as acute pulmonary vasoconstriction, adult respiratory distress syndrome, acute pulmonary edema, acute mountain sickness, post cardiac surgery acute pulmonary hypertension, persistent pulmonary hypertension in a newborn, perinatal aspiration syndrome, and asthma. For inhalation therapy, it is important that the NO gas mixture be free of the toxic gas $NO_2$ which can form inside compressed gas cylinders.

The present invention provides a simple method for the production of nitric oxide from a non-hazardous, gas-phase precursor. Without the need for high temperatures, strong acids, and aqueous solution, the invention allows NO to be produced from a small apparatus for portable, on-site use. The concentration of NO produced can be accurately controlled, thereby making the NO source highly useful as a calibration device for analytical instruments that measure nitric oxide in gases.

The foregoing example of the related art and limitations related therewith are intended to be illustrative and not exclusive. Other limitations of the related art will become apparent to those of skill in the art upon a reading of the specification and a study of the drawings.

SUMMARY

One aspect of this invention is a means to produce NO by exposing $N_2O$ to ultraviolet light.

Another aspect of the invention is to dilute NO produced by exposure of $N_2O$ to UV light into air, oxygen or a gas mixture for the purpose of inhalation therapy. For example, the NO/gas mixture could be administered to newborn babies, especially those born prematurely.

Another aspect of the invention is to dilute NO produced by exposure of N$_2$O to UV light with air, nitrogen or another gas for calibration of analytical instruments that measure NO such as nitric oxide monitors used to measure NO in ambient air, automotive exhaust and analyzers that measure NO in exhaled breath.

Another aspect of this invention is to control the concentration or mixing ratio of NO produced by controlling the UV light intensity, pressure, temperature, N$_2$O flow rate and/or diluent gas flow rate, with particular attention given to control of the UV light intensity.

Another aspect of this invention is to produce concentrations of gases other than NO at controlled levels by using different reagent gas sources.

Disclosed herein is a method for producing nitric oxide by exposing nitrous oxide (N$_2$O) to ultraviolet light in a controlled environment. This method has advantages over other methods of producing NO. For example, only one chemical reagent (N$_2$O) is required, and this reagent is relatively non toxic (used at mixing ratios of up to 50% in air as an anesthetic) and commercially available in small cartridges as a consumer product for making whipped cream. The only significant byproducts produced are nitrogen and oxygen, the major components of air. For applications where it is desirable or necessary to remove the unreacted N$_2$O, methods for the catalytic decomposition of N$_2$O into N$_2$ and O$_2$ have been developed. In this regard, reference is made to U.S. Pat. Nos. 5,314,673; 6,347,627; 6,429,168 and 6,743,404. The simplicity of the method described here provides for a compact, low power, portable NO source in which the concentration of NO produced is easily controlled.

The same apparatus designed for producing calibrated concentrations of NO in a diluent gas by photolysis of N$_2$O may, with either no or only minor modifications, be used to produce calibrated concentrations of other gases as well. For example, if N$_2$O is replaced with carbon dioxide (CO$_2$), the same apparatus may be used to produce controlled concentrations of carbon monoxide (CO). If N$_2$O is replaced with SF$_6$, calibrated concentrations of molecular fluorine (F$_2$) in a diluent gas can be produced. In fact, concentrations of many different gases may be produced by proper choice of the reagent gas.

These and other features and advantages of the disclosed method with the chosen components and the combination thereof, the mode and operation and use, as well become apparent from the following description, reference being made to the accompanying drawings that form a part of this specification wherein like reference characters designate corresponding parts in several views. The embodiments and features thereof are described and illustrated in conjunction with systems, tools and methods which are meant to exemplify and to illustrate, not being limiting in scope.

The following embodiments and aspects thereof are described and illustrated in conjunction with systems, tool and methods which are meant to be exemplary and illustrative, not limiting in scope. In various embodiments, one or more of the above described problems have been reduced or eliminated, while other embodiments are directed to other improvements.

Figure 1:
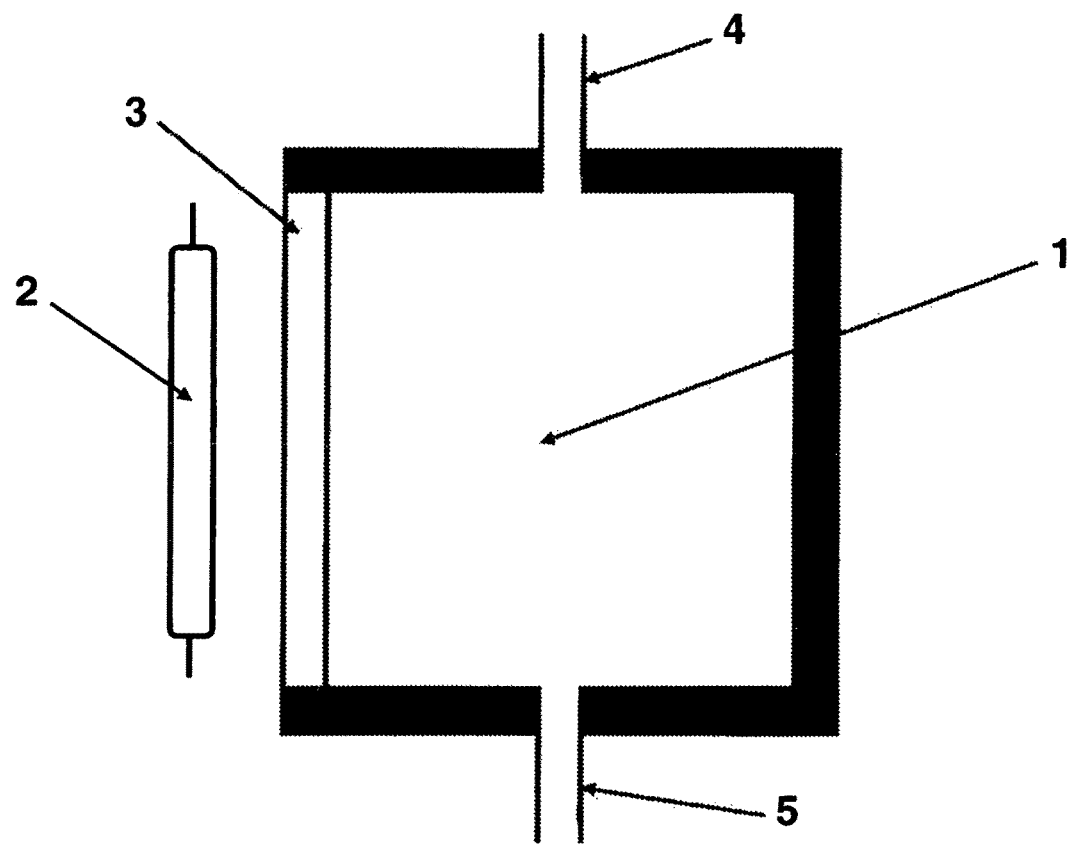
FIG. 1 is a schematic diagram of an apparatus used to produce NO by photolyzing N$_2$O.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION

In this method N$_2$O is photolyzed in the absence of ambient air to produce electronically excited oxygen atoms, which then react with N$_2$O to produce NO as follows:

$$N_2O + h\nu \rightarrow N_2 + O(^1D_2) \quad (1)$$

$$O(^1D_2) + N_2O \rightarrow N_2 + O_2 \quad (2)$$

$$\text{Net: } 2N_2O \rightarrow 2N_2 + O_2 \quad (3)$$

and $$N_2O + h\nu \rightarrow N_2 + O(^1D_2) \quad (4)$$

$$O(^1D_2) + N_2O \rightarrow 2NO \quad (5)$$

$$\text{Net: } 2N_2O \rightarrow 2NO + N_2 \quad (6)$$

Here, O($^1D_2$) is an electronically excited state of the oxygen atom. N$_2$O has a broad absorption band in the wavelength region 160-260 nm, and the quantum yield for reaction 1 is unity at wavelengths shorter than the thermodynamic limit of 230 nm (NASA, 2006). It is believed that the most efficient wavelengths for the conversion are between 170 to 190 nm, inclusive. In pure N$_2$O, O($^1D_2$) reacts with N$_2$O to form two sets of products, either N$_2$+O$_2$ (reaction 3) or 2 NO (reaction 5). The two sets of products are produced with yields of 41% and 59%, at 298 K, respectively based on the measured rate coefficients for reactions 3 and 5 (NASA, 2006).

Another possible fate of the O($^1D_2$) atom produced in reaction 1 is deactivation to the ground state according to the following reaction:

$$O(^1D_2) + M \rightarrow O + M \quad (7)$$

Here, M is any molecule or atom, principally N$_2$O. In reaction 7, a ground state oxygen atom is formed. It has been reported that less than 4% of O($^1D_2$) produced in the presence of N$_2$O is collisionally deactivated to ground state atoms (Wine and Ravishankara, 1982). To the extent that it is formed, the primary fate of this O atom is recombination to form molecular oxygen:

$$O + O + M \rightarrow O_2 + M \quad (8)$$

Again, M is any molecule or atom, principally N$_2$O.

The only byproducts produced in reactions 1-8 are N$_2$ and O$_2$, the principal components of air. Significantly, the reaction system does not directly produce the toxic gas nitrogen dioxide (NO$_2$). Potentially, nitrogen dioxide could be produced in the secondary reaction $$2NO + O_2 \rightarrow NO_2 \quad (9)$$

where the O$_2$ is derived from reaction 2 and to a much smaller extent from reaction 8. However, reaction 9 has a small rate coefficient and is second order in NO concentration, with the result that reaction conditions can be chosen where the concentration of $NO_2$ produced is insignificant. As an example, in inhalation therapy the concentration of NO administered is typically in the range 20-100 part per million (ppmv). In order to produce 100 ppmv NO in air with a 1% dilution of the $N_2O$/NO source gas into air, the concentration of NO in the $N_2O$ source gas would need to be 10,000 ppmv. The corresponding amount of oxygen produced in reaction 2 would be 3,500 ppmv. Using the rate coefficient of $1.9\ e^{-38}\ cm^6\ molec^{-2}\ S^{-2}$ at 298 K for reaction 9 (NBS, 1977), the half life for reaction of 10,000 ppmv NO in the presence of 3,500 ppmv $O_2$ is calculated to be 0.7 hours, and for a 10 second residence time in the photolysis chamber the $NO_2$ concentration produced is 40 ppmv, which after diluted into air is 0.4 ppmv. By comparison, the U.S. Occupational Safety and Health Administration permissible exposure limit (PEL) to $NO_2$ is 5 ppmv and 8 hour time weighted average (TWA) is 3 ppmv.

Referring first to FIG. 1, a reaction chamber 1 contains $N_2O$ gas or liquid. The reaction chamber 1 has been purged of substantially all of the ambient air by the $N_2O$ flowing into the chamber prior to the start of the reaction. Light from a UV lamp 3 passes through a window 2 into the test chamber. Reaction chamber 1 optionally has an inlet 4 for admitting the $N_2O$ gas or liquid and an exit 5 for removing reaction products and unreacted $N_2O$ gas or liquid. When the lamp is turned on, the NO concentration begins to increase inside the reaction chamber. The rate at which NO is produced increases with the density of $N_2O$ in the chamber and the UV light intensity. Optionally, lamp 3 may be placed inside reaction chamber 1, in which case window 2 is not required. It is understood that the reaction chamber itself is not required to produce NO provided that the lamp is surrounded by $N_2O$ gas or liquid.

Figure 2:
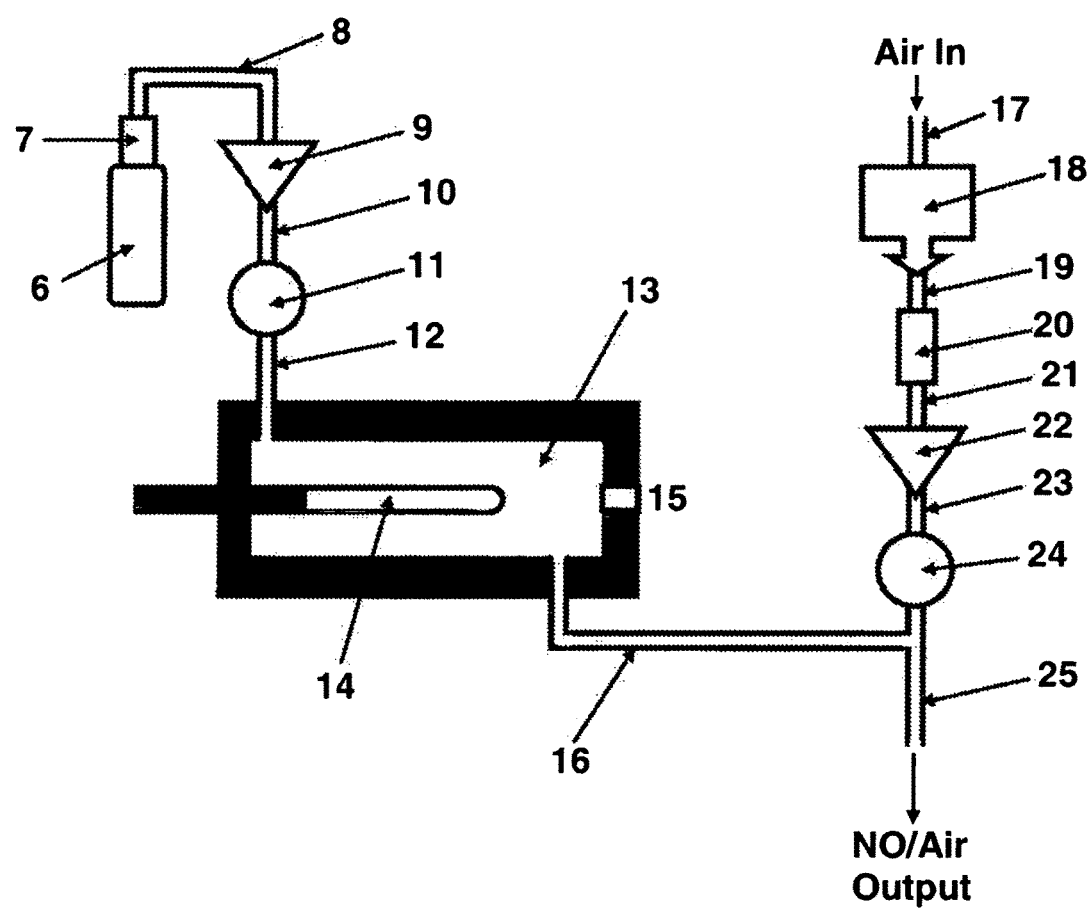
FIG. 2 is a schematic diagram of an apparatus used to produce a variable concentration of NO in a flowing gas stream.

Referring next to FIG. 2, a schematic diagram is provided of an actual apparatus used to produce and control the concentration of NO in a flowing stream of air. Nitrous oxide gas contained in $N_2O$ cartridge 6 passes through pressure regulator 7, through connecting tube 8, through flow controller 9, through connecting tube 10, through flow meter 11, through connecting tube 12, and into reaction chamber 13. Ultraviolet light from UV lamp 14 causes NO to be formed inside chamber 13. UV light from lamp 14 is monitored by photodiode 15. In the depicted embodiment, a low pressure mercury lamp, which has a weak emission near 185 nm in addition to its principal emission at 254 nm, is used. The radiation at 185 nm, where the $N_2O$ absorption cross section is high, is responsible for the production of NO. Other types of UV emitting lamps could be used as well, including a high pressure mercury lamp, xenon arc lamp, hydrogen lamp, deuterium lamp and other known or later developed UV emitting sources. A feedback loop in which the voltage to the UV lamp is pulse width modulated is used to maintain a constant signal at photodiode 15 so that NO is produced at a constant rate.

Unreacted $N_2O$, NO and other reaction products flow out of reaction chamber 13, into connecting tube 16, and are mixed with a flow of NO-scrubbed air in tube 25. The NO/air mixture, having a substantially constant NO concentration, exits tube 25 and may be sampled by a NO measurement device for the purpose of calibration. The NO-scrubbed air is produced by drawing in ambient air by air pump 18 through inlet 17. The air then passes through connecting tube 19, through NO scrubber 20, through connecting tube 21, through flow controller 22, through connecting tube 23, through flow meter 24 and into tube 25. For a fixed lamp intensity, the mixing ratio of NO exiting tube 25 may be varied by varying the diluent air flow rate using flow controller 22. Because the absorption of UV light is nearly optically thick (nearly every photon of sufficient energy to cause photolysis is absorbed by $N_2O$), the output mixing ratio of NO is nearly insensitive to the flow rate of $N_2O$.

The apparatus of FIG. 2 may be used to produce controlled mixing ratios of other gases in a dilute gas as well. For example, if the $N_2O$ cartridge of FIG. 2 is replaced by a $CO_2$ cartridge or other source of $CO_2$, carbon monoxide and molecular oxygen may be produced by the following mechanism:

$$2\times(CO_2+h\nu \rightarrow CO+O) \qquad (10)$$

$$O+O+M \rightarrow O_2+M \qquad (11)$$

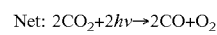
Net: $2CO_2+2h\nu \rightarrow 2CO+O_2$

Thus, the photolysis reaction can be used to produce a controlled concentration of CO and $O_2$. Again, the $CO_2$ flowing into the reaction chamber 1 purges the reaction chamber of substantially all of the ambient air. Although a low pressure mercury lamp can be used to produce low concentrations of CO according to this mechanism, a preferred lamp would be a hydrogen or deuterium lamp, because the lamp emission spectrum better overlaps that of the $CO_2$ absorption spectrum.

Similarly, if the $N_2O$ source is replaced with a source of sulfur hexafluoride ($SF_6$), then a controlled concentration of $SF_4$ and $F_2$ could be produced according to the sequence of reactions:

$$SF_6+h\nu \rightarrow SF_5+F \qquad (12)$$

$$SF_5+F \rightarrow SF_4+F_2 \qquad (13)$$

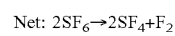
Net: $2SF_6 \rightarrow 2SF_4+F_2$

Many other reagents can be photolyzed with ultraviolet light. In many of these, the presence of ambient air will cause the photolysis to produce a gas product or products such as ozone. However, if the photolysis in done in the absence of ambient air, a different, and possibly more desirable gas product will be formed. As would be known by the practitioner of the art, a number of gases could be used to produce either the gas products discussed above, or other reaction products, the key being that the concentration of the gas product is controlled by a combination of lamp intensity, flow rate of gas through the photolysis chamber and flow rate of diluent gas. The apparatus of FIG. 2 can thus be used to produce controlled concentrations of specific gases for many applications including calibration of analytical instruments.

EXAMPLE 1

Figure 3:
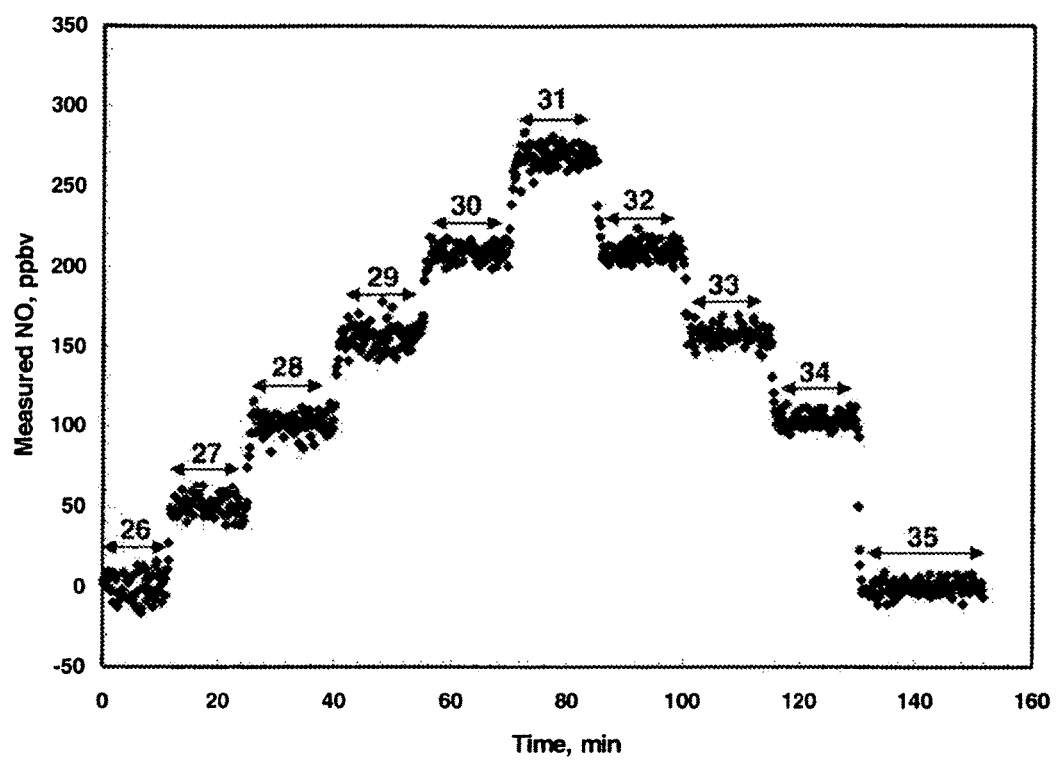
FIG. 3 is a chart of data showing the measured concentrations of NO produced using the apparatus of FIG. 1.

Referring next to FIG. 3, experimental results are shown for production of NO at different mixing ratios using an apparatus described by the schematic diagram of FIG. 2. The vertical axis is the mixing ratio of NO in parts-per-billion by volume (ppbv) measured using a 2B Technologies Model 400 Nitric Oxide Monitor™. The horizontal axis is time in minutes. The $N_2O$ volumetric flow rate is 18 cc/min, the air volumetric flow rate is 940 cc/min, the temperature of the reaction chamber is thermostated at 37° C., and the pressure in the reaction chamber is 848 mbar. The UV lamp used was a low pressure mercury lamp with greater than 95% of the surface of the lamp painted to be opaque. The average intensity of the lamp was varied by pulse width modulation to produce NO concentrations in the range 0-270 ppbv as summarized in Table 1.

TABLE 1

| Region of FIG. 3 | Time Interval | % Pulse Width Modulation | Average Measured NO Mixing Ratio ± Standard Error of the Mean, ppbv |
|---|---|---|---|
| 26 | 0.0-11.2 | 0.0 | 0.2 ± 0.9 |
| 27 | 11.8-25.0 | 3.2 | 50.7 ± 0.7 |
| 28 | 25.7-39.8 | 6.4 | 102.3 ± 0.6 |
| 29 | 41.3-54.7 | 9.6 | 156.3 ± 0.8 |
| 30 | 55.8-69.8 | 12.8 | 209.1 ± 0.5 |
| 31 | 71.2-85.0 | 16.0 | 269.1 ± 0.7 |
| 32 | 86.2-99.8 | 12.8 | 209.5 ± 0.6 |
| 33 | 101.0-115.0 | 9.6 | 156.7 ± 0.6 |
| 34 | 116.2-129.5 | 6.4 | 103.6 ± 0.5 |
| 35 | 131.3-151.5 | 0.0 | −0.1 ± 0.4 |

EXAMPLE 2

In a second example, the apparatus of FIG. 2 was used to generate different concentrations of CO in air by using $CO_2$ as the reagent gas and varying the UV lamp intensity. In this example, the $N_2O$ cartridge 6 of FIG. 2 was replaced with a $CO_2$ cartridge, and the NO scrubber was replaced with a hopcalite scrubber to remove CO. The low pressure mercury lamp was replaced with an unpainted mercury lamp because the extinction coefficient for absorption of the 185 nm emission line of mercury is approximately 400 times less for $CO_2$ as compared to $N_2O$. Also, the volume of the reaction chamber was increased from 4.1 $cm^3$ to 118.4 $cm^3$. A flow of 72-83 $cm^3$/min of $CO_2$ passed through the reaction chamber 13 and mixed with a flow rate of approximately 1 liter/minute of air. The output of the apparatus was analyzed for CO by use of a Thermo Electron Corporation Model 48i CO Gas Analyzer. The results are given in Table 2, which shows that CO is produced in the apparatus and that the concentration produced can be varied by varying the lamp intensity.

TABLE 2

| Run | $CO_2$ Flow Rate $cm^3$/min | Lamp Duty Cycle, % | Lamp Intensity Arbitrary Units | Measured CO Concentration, ppbv |
|---|---|---|---|---|
| 1 | 72 | 30 | 4280 | 209 |
| 2 | 74 | 30 | 4280 | 200 |
| 3 | 74 | 30 | 4280 | 199 |
| 4 | 77 | 30 | 4280 | 210 |
| Average: | 74 | 30 | 4280 | 205 |
| 1 | 81 | 49 | 6400 | 285 |
| 2 | 79 | 49 | 6400 | 295 |
| Average: | 80 | 49 | 6400 | 290 |
| 1 | 79 | 78 | 8230 | 400 |
| 2 | 87 | 72 | 8230 | 395 |
| Average: | 83 | 75 | 8230 | 398 |

While a number of exemplary aspects and embodiments have been discussed above, those of skill in the art will recognize certain modifications, permutations, additions and sub-combinations therefore. It is therefore intended that the following appended claims hereinafter introduced are interpreted to include all such modifications, permutations, additions and sub-combinations are within their true spirit and scope. Each apparatus embodiment described herein has numerous equivalents.

CITED LITERATURE

NASA (2006) Chemical Kinetics and Photochemical Data for Use in Stratospheric Modeling, Evaluation Number 15, JPL Publication 06-2.
Wine, P. H. and A. R. Ravishankara (1982) *Chemical Physics* 69, 365-373.
NBS (1977) NBS Special Publication 513, Reaction Rate and Photochemical Data for Atmospheric Chemistry, 1977.

The invention claimed is:

1. A method of synthesizing nitric oxide (NO) which comprises:
   providing a flow of nitrous oxide ($N_2O$) into a reaction chamber, the chamber being substantially free of ambient air,
   exposing the $N_2O$ to ultraviolet light at wavelengths shorter than 230 nm for an amount of time sufficient to allow a concentration of NO of between 0.05 ppmv and 100 ppmv to be formed in a resultant gas mixture, the amount of time being calculable using the flow rate and concentration of $N_2O$, the flow rate and concentration of a diluent gas, chamber volume, intensity of the ultraviolet light, absorption cross section for $N_2O$ and quantum yield for NO production, and
   wherein the resultant gas mixture has a concentration of no more than 0.4% $NO_2$.

2. The method of claim 1 wherein the wavelength is with the range of 160-230 nm.

3. The method of claim 2 wherein a mercury lamp is a source of ultraviolet light.

4. The method of claim 1, further comprising the steps of continuously flowing $N_2O$ into the reaction chamber at a rate chosen to achieve a given residence time in the reaction chamber and flowing NO, unreacted $N_2O$ and other reaction products out of the reaction chamber.

5. The method of claim 1, wherein a source of ultraviolet light is a mercury lamp.

6. The method of claim 5 wherein the mercury lamp is inside the reaction chamber.

7. The method of claim 1 further comprising the step of varying an intensity or duty cycle of the ultraviolet light thereby varying the concentration of NO produced.

8. A method of synthesizing nitric oxide (NO) for a gas mixture, the method comprising the steps of:
   providing a flow of nitrous oxide ($N_2O$) into a reaction chamber until the reaction chamber is purged of substantially all ambient air;
   exposing the flow of $N_2O$ to ultraviolet light in the reaction chamber provided by a light source;
   forming NO from the exposure of the flow of $N_2O$ to the ultraviolet light to create a $N_2O$/NO source gas;
   collecting the $N_2O$/NO source gas which exits the reaction chamber; and
   mixing the $N_2O$/NO source gas with a flow of a diluent gas to form the gas mixture;
   wherein the gas mixture that results has a concentration of NO between approximately 1-270 ppbv, and a concentration of no more than 0.4% $NO_2$.

9. The method of claim 8, wherein the flow of $N_2O$ entering the reaction chamber is approximately 18 cc/min, and the reaction chamber has a volume of approximately 4.1 cc, such that $N_2O$ has an average exposure time in the reaction chamber of approximately 13.7 seconds.

10. The method of claim 8, wherein the reaction chamber has an initial temperature of approximately 37° C. and pressure of approximately 850 mbar.

11. The method of claim 8, wherein the flow of $N_2O$ entering the reaction chamber is approximately 18 cc/min, and the reaction chamber has a volume of approximately 4.1 cc, such that $N_2O$ has an average exposure time in the reaction chamber of approximately 13.7 seconds; and wherein the reaction chamber has an initial temperature of approximately 37° C. and pressure of approximately 850 mbar.

12. The method of claim 11, wherein the diluent gas is air scrubbed of NO before mixing with the $N_2O$/NO source gas, and the flow of the diluent gas is approximately 940 cc/min.

13. The method of claim 12, wherein the light source has an emission near 185 nm, a pulse width modulation up to approximately 16.0%, and is painted for approximately 95% opaqueness.

14. The method of claim 11, wherein the light source has an emission near 185 nm, a pulse width modulation up to approximately 16.0%, and is painted for approximately 95% opaqueness.

15. The method of claim 8, wherein the diluent gas is air scrubbed of NO before mixing with the $N_2O$/NO source gas.

16. The method of claim 8, wherein the flow of the diluent gas is approximately 940 cc/min.

17. The method of claim 8, wherein the diluent gas is air scrubbed of NO before mixing with the $N_2O$/NO source gas, and the flow of the diluent gas is approximately 940 cc/min.

18. The method of claim 17, wherein the light source has an emission near 185 nm, a pulse width modulation up to approximately 16.0%, and is painted for approximately 95% opaqueness.

19. The method of claim 8, wherein the light source has an emission near 185 nm.

20. The method of claim 8, wherein the light source has a pulse width modulation up to approximately 16.0%.

21. The method of claim 8, wherein the light source is painted for approximately 95% opaqueness.

22. The method of claim 8, wherein the light source has an emission near 185 nm, a pulse width modulation up to approximately 16.0%, and is painted for approximately 95% opaqueness.

23. A method of synthesizing nitric oxide (NO) mixed into a diluent gas to form a resultant gas, the method comprising:
flowing nitrous oxide ($N_2O$) into a reaction chamber, the reaction chamber substantially free of ambient air;
exposing the $N_2O$ to ultraviolet light emitted from a light source at wavelengths shorter than 230 nm to form photolysis products, the $N_2O$ photolyzing to form the products NO and $N_2$ or $N_2$ and $O_2$ at about a 3:2 ratio;
flowing the photolysis products and unreacted $N_2O$ out of the reaction chamber; and
mixing the photolysis products and unreacted $N_2O$ with a flow of the diluent gas to produce the resultant gas, the diluent gas scrubbed of NO before mixing;
wherein the resultant gas has a concentration of NO>0 and ≤100 ppmv and a concentration of $NO_2$≤0.4 ppmv; and
wherein the concentration of NO in the resultant gas is controlled by varying at least one of the intensity of the light source, the flow of $N_2O$ and the flow of the diluent gas.

24. The method of claim 23, wherein the wavelengths of the ultraviolet light are between 160 and 230 nm.

25. The method of claim 24, wherein the light source is a mercury lamp positioned inside the reaction chamber.

26. The method of claim 23, wherein the intensity of the light source is varied by pulse width modulation.

27. The method of claim 23, wherein the concentration of NO is between 20 and 100 ppmv.

28. A method of synthesizing nitric oxide (NO) mixed into a diluent gas to form a resultant gas, the method comprising:
flowing nitrous oxide ($N_2O$) into a reaction chamber, the reaction chamber substantially free of ambient air;
exposing the $N_2O$ to ultraviolet light emitted from a light source at wavelengths shorter than 230 nm to form photolysis products, the $N_2O$ photolyzing to form the products NO and $N_2$ or $N_2$ and $O_2$ at about a 3:2 ratio, the reaction chamber sized so that absorption of the ultraviolet light is optically thick;
flowing the photolysis products and unreacted $N_2O$ out of the reaction chamber; and
mixing the photolysis products and unreacted $N_2O$ with a flow of the diluent gas to produce the resultant gas, the diluent gas scrubbed of NO before mixing;
wherein the resultant gas has a concentration of NO>0 and ≤100 ppmv and a concentration of $NO_2$≤0.4 ppmv; and
wherein the concentration of NO in the resultant gas is controlled by varying at least one of the intensity of the light source, the flow of $N_2O$ and the flow of the diluent gas.

* * * * *